(12) United States Patent
Lo et al.

(10) Patent No.: US 8,114,016 B2
(45) Date of Patent: Feb. 14, 2012

(54) MODULAR SURGERY RETRACTOR SYSTEM

(75) Inventors: Janzen Lo, Allentown, PA (US); Yufei Xiang, Allentown, PA (US)

(73) Assignee: GoMedica Technologies Co., Ltd., Changzhou, Jiangsu Provience (CN)

( * ) Notice: Subject to any disclaimer, the term of this patent is extended or adjusted under 35 U.S.C. 154(b) by 382 days.

(21) Appl. No.: 12/351,955

(22) Filed: Jan. 12, 2009

(65) Prior Publication Data

US 2009/0227845 A1    Sep. 10, 2009

Related U.S. Application Data

(60) Provisional application No. 61/033,532, filed on Mar. 4, 2008.

(51) Int. Cl.
*A61B 1/32* (2006.01)
(52) U.S. Cl. ...................................................... 600/202
(58) Field of Classification Search ................. 600/215, 600/216, 219, 231–233, 201, 213
See application file for complete search history.

(56) References Cited

U.S. PATENT DOCUMENTS

| | | | | |
|---|---|---|---|---|
| 4,156,424 | A | * | 5/1979 | Burgin ........................... 600/213 |
| 5,813,978 | A | * | 9/1998 | Jako ............................. 600/201 |
| 2005/0113644 | A1 | * | 5/2005 | Obenchain et al. ............ 600/222 |
| 2007/0073111 | A1 | * | 3/2007 | Bass .............................. 600/215 |
| 2008/0188718 | A1 | * | 8/2008 | Spitler et al. .................. 600/213 |

* cited by examiner

*Primary Examiner* — Eduardo C Robert
*Assistant Examiner* — Summer Kostelnik
(74) *Attorney, Agent, or Firm* — Kohn & Associates, PLLC (57) ABSTRACT

A reconfigurable modular retractor system including a set of interchangeable body modules, the body modules including mechanisms for forming retractors and slot mechanisms for connecting blades, and blades including locking mechanisms for locking inside the slot mechanisms. A method of using the retractor system by forming a retractor by using at least one body module, attaching blades to the body module, inserting the retractor into a surgical area, retracting tissue, removing retraction from the tissue, and removing the retractor.

29 Claims, 11 Drawing Sheets

MODULAR SURGERY RETRACTOR SYSTEM

CROSS-REFERENCE TO RELATED APPLICATIONS

This application claims the benefit of priority under 35 U.S.C. Section 119(e) of U.S. Provisional Patent Application No. 61/033,532, filed Mar. 4, 2008, which is incorporated herein by reference.

BACKGROUND OF THE INVENTION (1) Field of the Invention

The present invention relates to a surgical retractor system. In particular, the present invention relates to a surgical retractor system with interchangeable modules.

(2) Description of the Prior Art

Surgical retractors are used to maintain exposure to organs and tissues once an incision in a patient has been made. The retractor is inserted in the incision and then adjusted as needed to move tissues and organs so that surgery can be performed.

There are presently many different sets of retractors because each surgeon can have different training or preferences and certain retractors are used for different surgical procedures. Thus, hospitals currently stock many different types of retractors as per each surgeon's preferences.

For example, U.S. Pat. No. 6,206,828 to Wright discloses a retractor with detachable blades, wherein the retractor is adjustable with a rack and pinion mechanism and the blades are secured by a latch. U.S. Pat. No. 6,322,500 to Sikora, et al. discloses retractor blades that are removable and disposable, however, this retractor is for use in cardiac surgery and is not used for orthopedic surgery. U.S. Patent Application No. 2005/0234304 to Dewey, et al. discloses a retractor wherein multiple blade modules (intermediate retractors) can be added to the basic retractor to increase tissue retraction capabilities in more than two directions. U.S. Patent Application No. 2007/0073111 to Bass discloses a retractor wherein the blades can be detached and the retractor is adjustable with a rack and pinion mechanism.

There is a need for a single modular retractor system that can be used for many different types of surgeries, streamline training of doctors, and reduce the need for hospitals to carry multiple types of retractors, as each has different size variations therefore enlarged inventory burden for hospitals.

SUMMARY OF THE INVENTION

The present invention provides for a reconfigurable modular retractor system including a set of interchangeable body modules, the body modules including mechanisms for forming retractors and slot mechanisms for connecting blades, and blades including locking mechanisms for locking inside the slot mechanisms.

The present invention also provides for a method of using the retractor system by forming a retractor by using at least one body module, attaching blades to the body module, inserting the retractor into a surgical area, retracting tissue, removing retraction from the tissue, and removing the retractor.

BRIEF DESCRIPTION ON THE DRAWINGS

Other advantages of the present invention will be readily appreciated as the same becomes better understood by reference to the following detailed description when considered in connection with the accompanying drawings, wherein.

DETAILED DESCRIPTION

Figure 1:
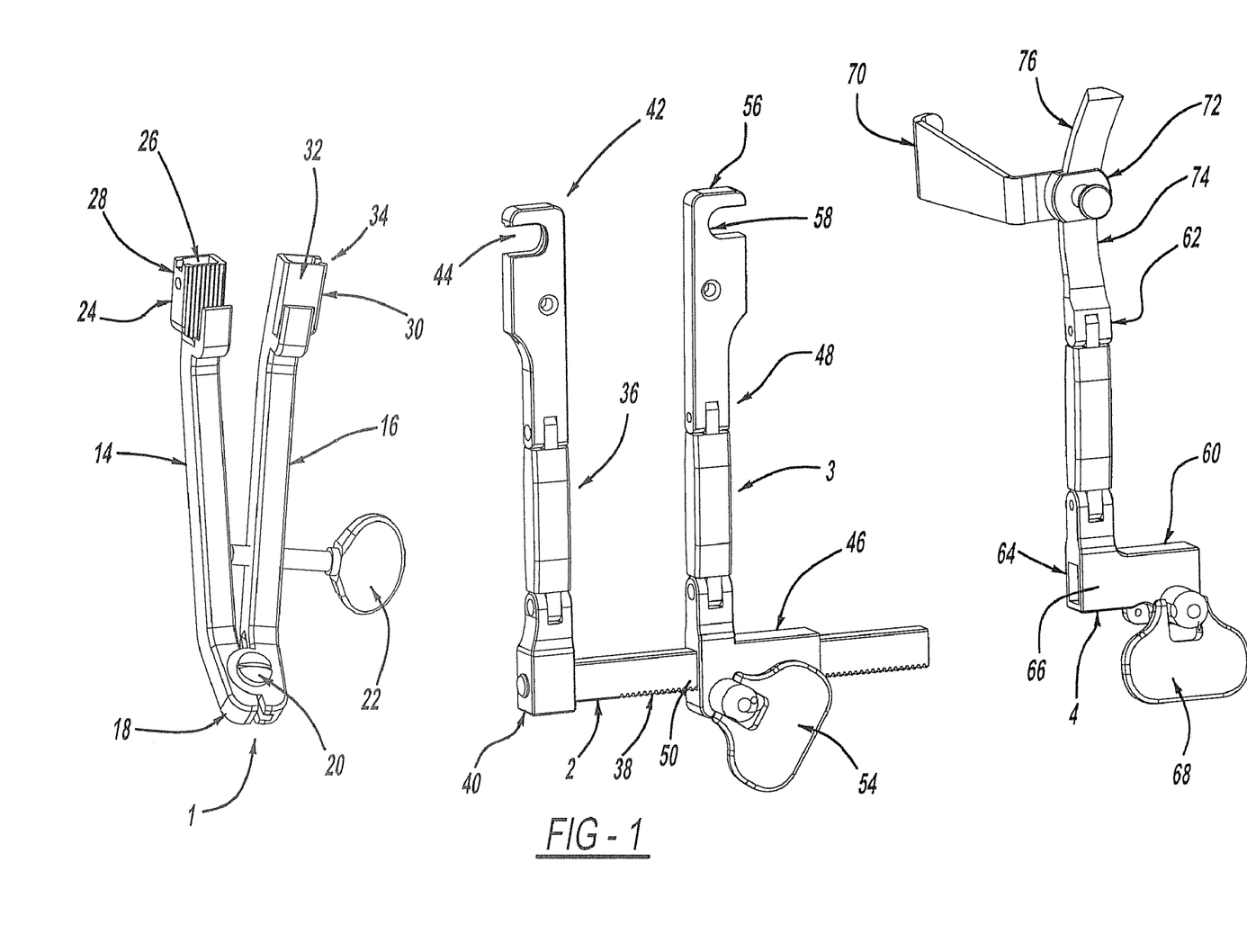
FIG. 1 is a three-dimensional representation of the body modules 1, 2, 3, and 4 of the modular retractor system.
Figure 2:
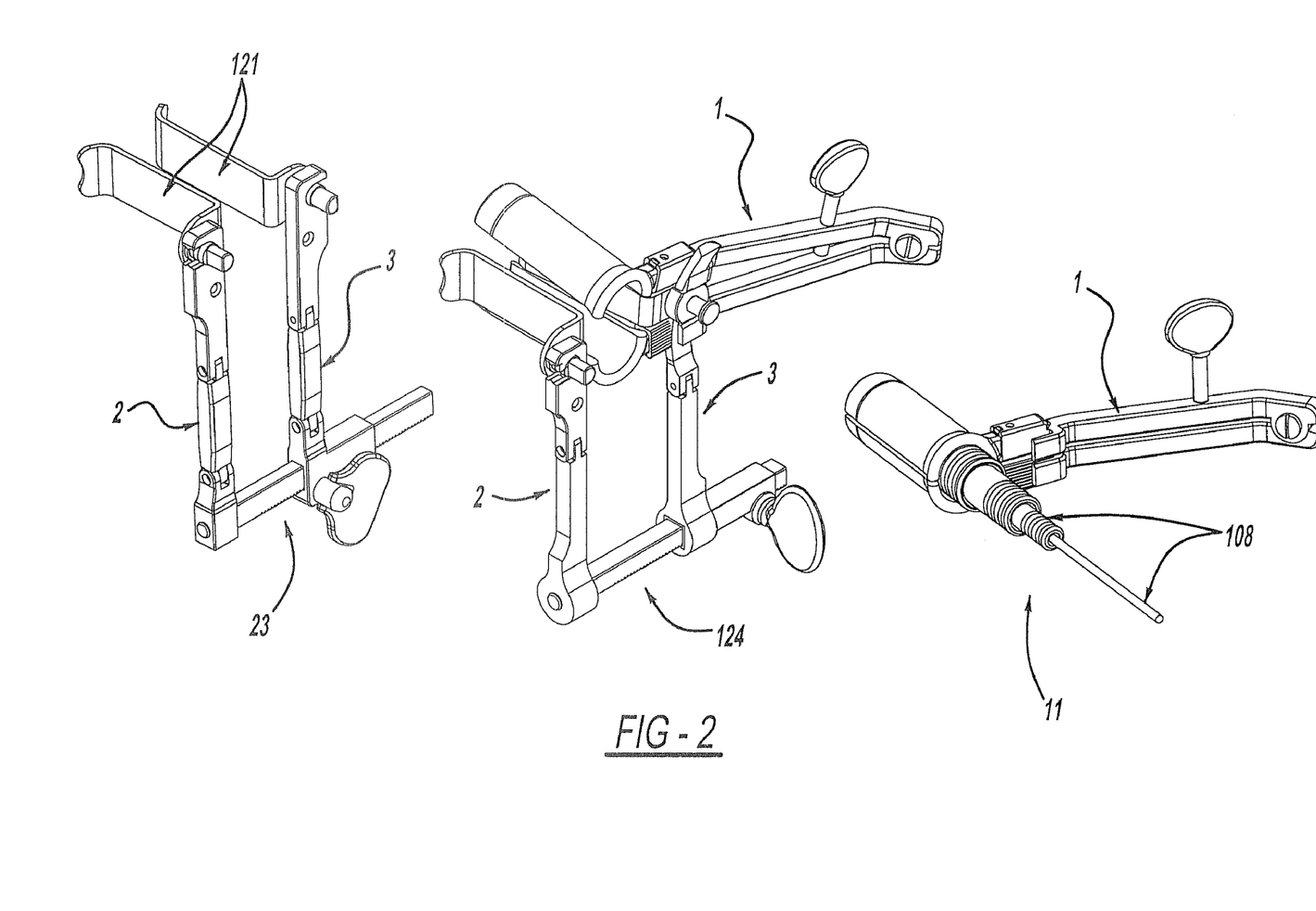
FIG. 2 is a three-dimensional representation of the retractors 12, 124, and 11 formed by the body modules.

The present invention provides a reconfigurable modular retractor system shown generally at 10 in FIG. 1 and includes body modules 1, 2, 3, 4, and 5. These body modules 1, 2, 3, 4, and 5 can attach together along with detachable blades 12 and 121 to form retractors 23 (providing one directional retraction), 124 (providing two directional retraction), 11 (providing tubular retraction) as shown in FIG. 2, and 25 (providing two directional retraction) as shown in FIGS. 4-7. Optionally, body module 6 can be used alone as part of body module 5.

Each of the body modules 1, 2, 3, 4, 5, and 6 are discussed separately first and how they are connected together subsequently. Preferably, the body modules are made of a biocompatible metal that can be sterilized after use in a patient. The body modules can also be made of non-biocompatible materials. The body modules can also be made of a sterilizable plastic or any other suitable material. Each of the pieces of the system can be color coded for easy identification and configuration by surgeons and other medical practitioners.

Figure 3:
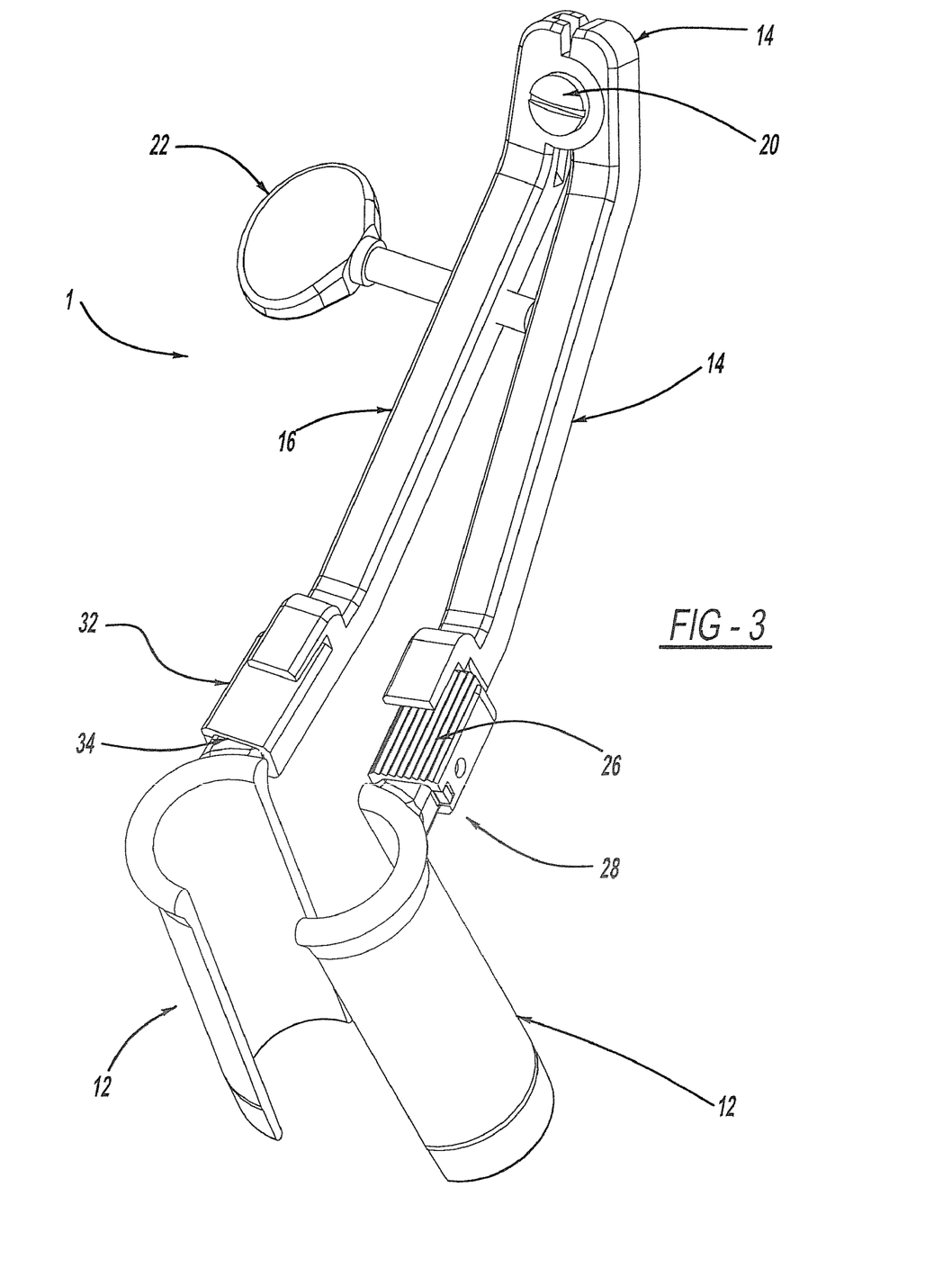
FIG. 3 is a three-dimensional representation of body module 1 with blades.

Body module 1 includes arms 14 and 16 attached at a proximal end 18 by a connecting mechanism 20, and is also shown in detail in FIG. 3. The connecting mechanism 20 can be a screw or a pin, or any other suitable mechanism that will allow for slight rotation of the arms 14 and 16. Essentially, the connecting mechanism 20 is the pivot point of the arms 14 and 16. Body module 1 also includes an adjusting mechanism 22 for adjusting the amount of space between the arms 14 and 16. The adjusting mechanism 22 is operatively and adjustably attached to each of arms 14 and 16. For example, the adjusting mechanism 22 can be a winged screw that is rotated in order to move arms 14 and 16 closer or farther away from each other. The adjusting mechanism is positioned in any suitable place along body module 1 in order to adjust arms 14 and 16. Arms 14 and 16 can be of any suitable length. Arm 14 includes a distal end 24 having a grooved slot 26 for receiving and retaining a toothed surface 74 of body module 4, further discussed below, and a blade receiving slot 28 for receiving a blade 12. Arm 16 includes a distal end 30 having a smooth slot 32 for receiving a smooth surface 76 of body module 4, also further discussed below, as well as a blade receiving slot 34 for receiving a blade 12.

Body module 2 includes arm 36 and perpendicular thereto arm 38 operatively connected at a proximal end 40. Arm 36 includes at its distal end 42 a blade receiving slot 44 for receiving a blade 121. Arm 38 is optionally toothed to operate as part of a rack and pinion system with body modules 3 and 4. This operating feature is further described below. Arm 38 can include any other suitable features to allow for movement of another body module along its length. Arms 36 and 38 can be of any suitable length.

Body module 3 includes a base 46 perpendicular to an arm 48. Base 46 includes a slot 50 wherein arm 38 of body module 2 can be inserted, and an adjusting mechanism 52 to adjust body module 3 along arm 38 of body module 2. The adjusting mechanism 52 can include any suitable locking device 54 to maintain the position of body module 3 along body module 2. For example, the adjusting mechanism 52 can be a pinion matching the toothed arm 38 to operate as a rack and pinion system, and the locking device 54 can be a wing. When the wing is flipped upwards, body module 3 moves along arm 38 of body module 2, and when the wing is flipped downwards, body module 3 is locked in position along arm 38 of body module 2. Arm 48 includes at its distal end 56 a blade receiving slot 58 for receiving a blade 121. When a blade 121 is in the blade receiving slot 58, it preferably is perpendicular to both the base 46 and the arm 48.

Body module 4 includes a base 60 perpendicular to an arm 62. Base 60 is similar in structure to base 46, and includes a slot 64 wherein arm 38 of body module 2 can be inserted, and an adjusting mechanism 66 to adjust body module 4 along arm 38 of body module 2. The adjusting mechanism 66 can include any suitable locking device 68 to maintain the position of body module 4 along body module along body module 2, and can be the rack and pinion system with wing as described above. Arm 62 includes a blade 70 that is optionally removably attached perpendicular to arm 62 and angled backward at a distal end 72. Below the distal end 72 of arm 62 is a toothed surface 74 for receiving and locking the grooved slot 26 of body module 1. Above the distal end 72, and slightly angled forwards, there is operatively attached a smooth surface 76 for receiving slot 32 of body module 1 such that slot 32 is slidable along the smooth surface 76.

Figure 15:
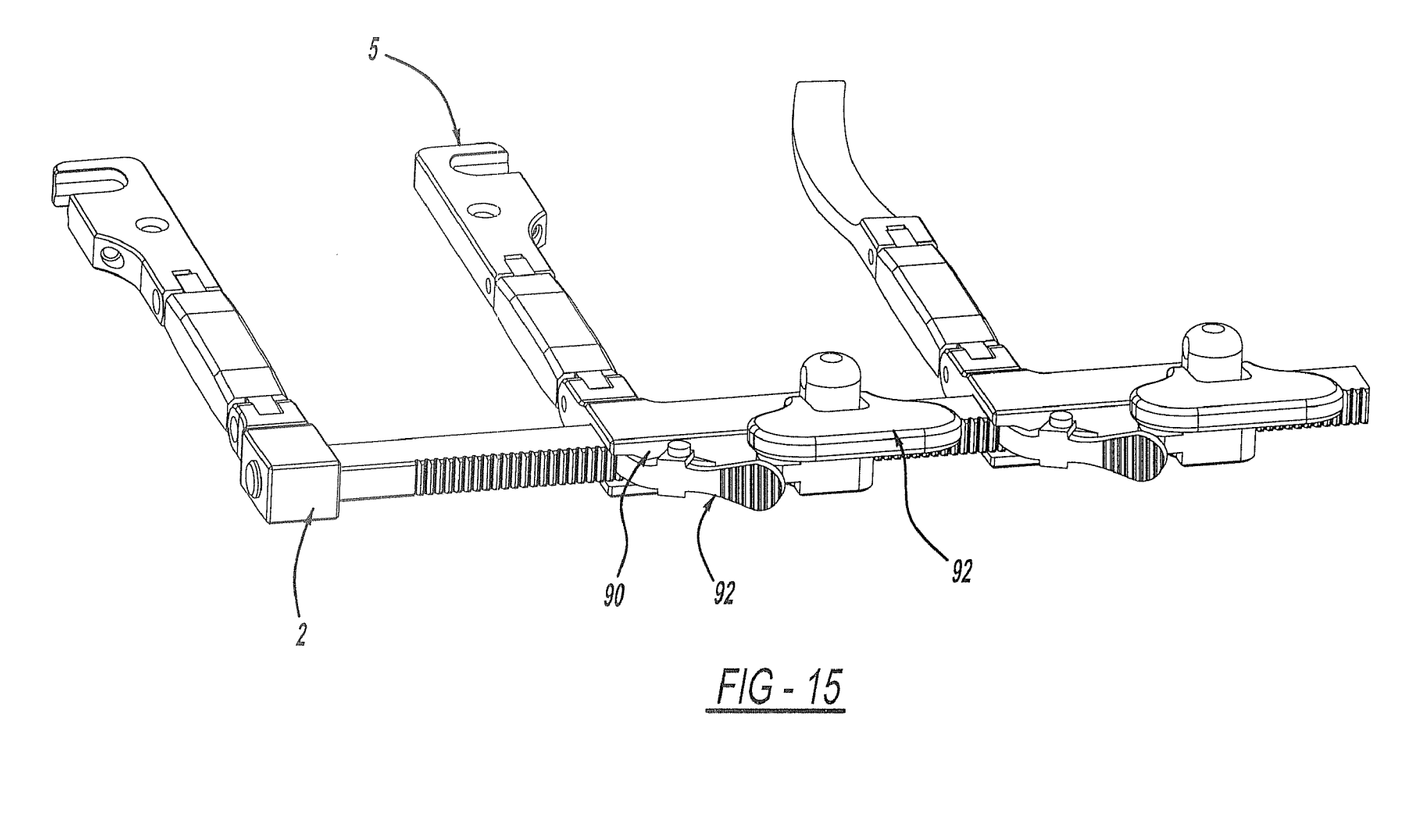
FIG. 15 is a photograph of the locking mechanism.

Body module 5 is shown in FIGS. 4-7 and includes a base 84 perpendicular to and removably attached to an arm 86 (also body module 6). Base 84 includes a slot 50 wherein arm 38 of body module 2 can be inserted, and an adjusting mechanism 90 to adjust body module 5 along arm 38 of body module 2. The adjusting mechanism 90 can include any suitable locking device 92 to maintain the position of body module 5 along body module 2. For example, the adjusting mechanism 90 can be a pinion matching the toothed arm 38 to operate as a rack and pinion system, and the locking device 92 can be a wing. When the wing is flipped upwards, body module 5 moves along arm 38 of body module 2, and when the wing is flipped downwards, body module 5 is locked in position along arm 38 of body module 2. The locking device 92 is further shown in FIG. 15. Arm 86 includes at its distal end 94 a blade receiving slot 96 for receiving a blade 121. When a blade 121 is in the blade receiving slot 96, it preferably is perpendicular to both the base 84 and the arm 86. The distal end 94 further includes a screw differentiating mechanism 98 for adjusting two blades 12 in a direction perpendicular to the blades 121 of arm 36 of body module 2 and arm 86 of body module 5. The screw differentiating mechanism 98 includes two blade receiving slots 100 (alternatively a slide mechanism 100) movably attached along a screw 102 and 102' (one is right hand screw and another is left hand screw). Turning of a wheel 104 causes screws 102 and 102' to rotate and move blades 12 in connection slots 100 closer or farther apart. The screw differentiating mechanism also includes a screw locking mechanism 106 to maintain blades 12 in place. The locking mechanism 106 can be located on screw 102, 102' itself that can hold the two blades in position.

Figures 6, 7:
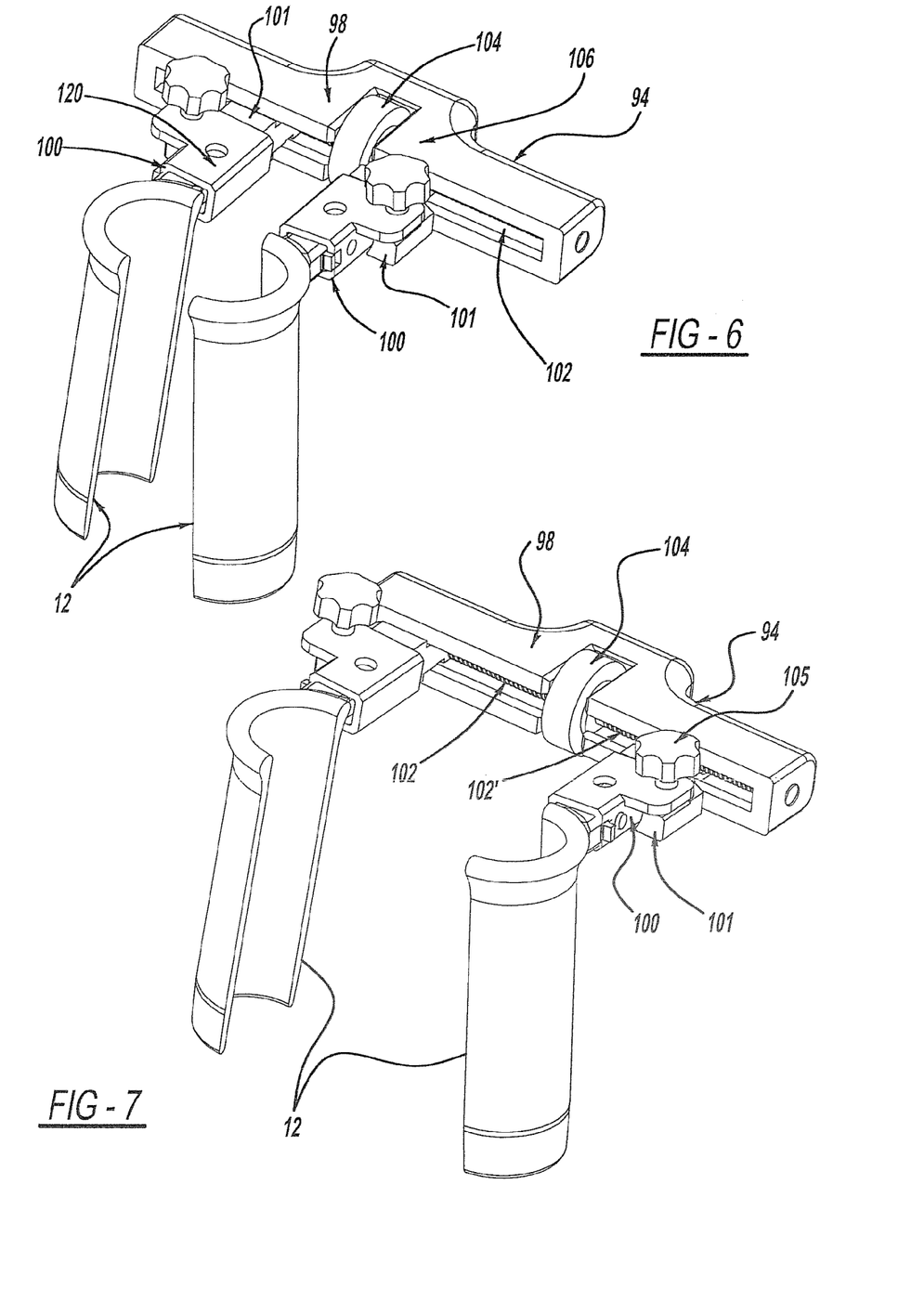
FIG. 6 is a close-up three-dimensional representation of a screw differentiating mechanism.
FIG. 7 is a close-up three-dimensional representation of the screw differentiating mechanism.
Figures 8, 9:
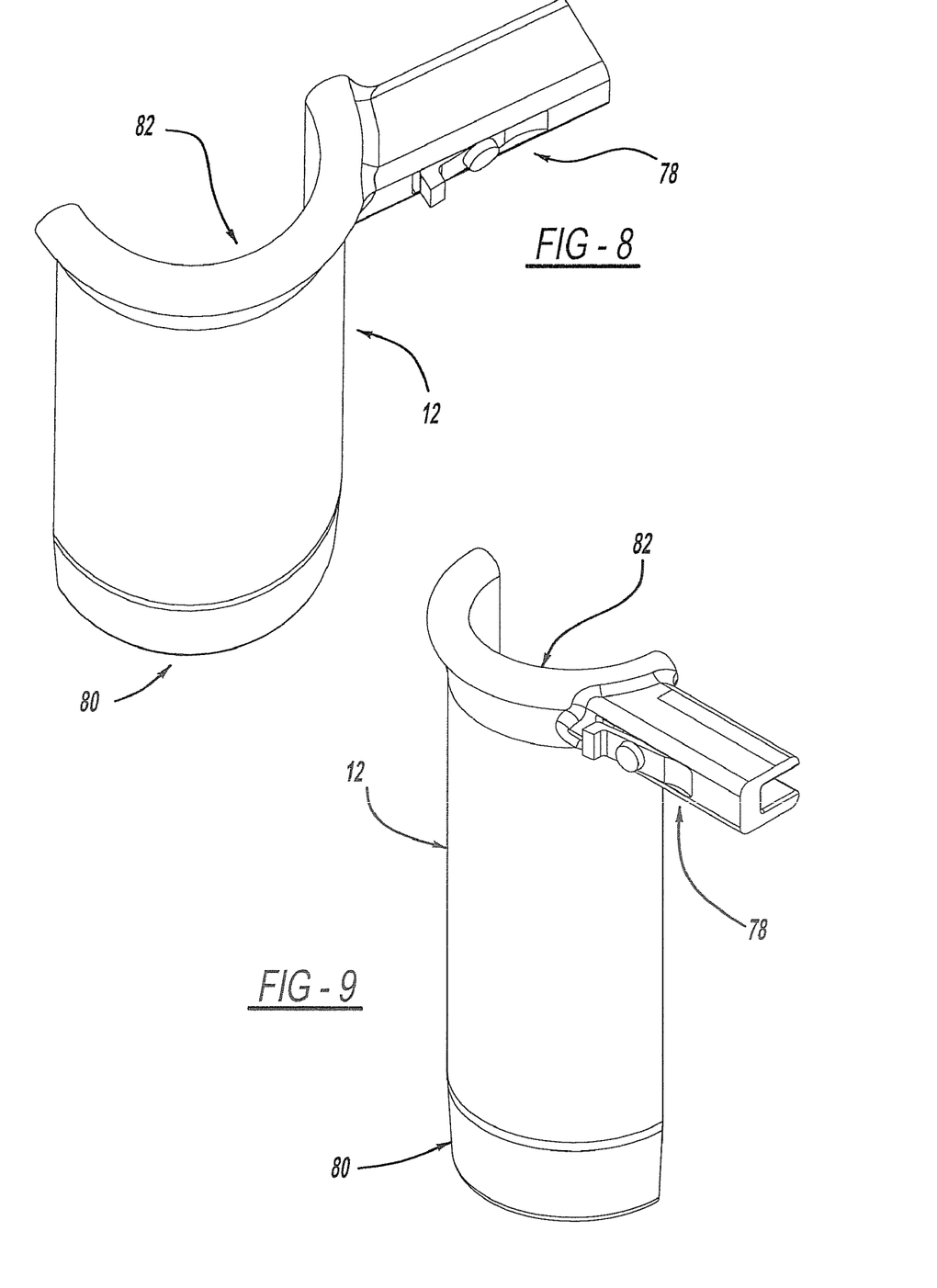
FIG. 8 is a three-dimensional representation of a blade.
FIG. 9 is a three-dimensional representation of a blade.
Figure 10:
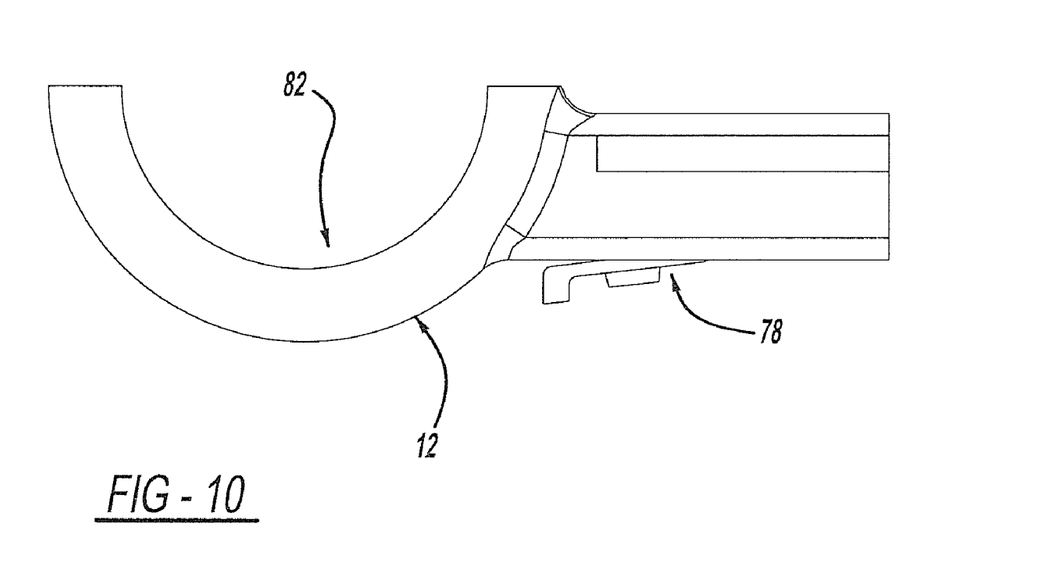
FIG. 10 is a top view of a blade.
Figure 11:
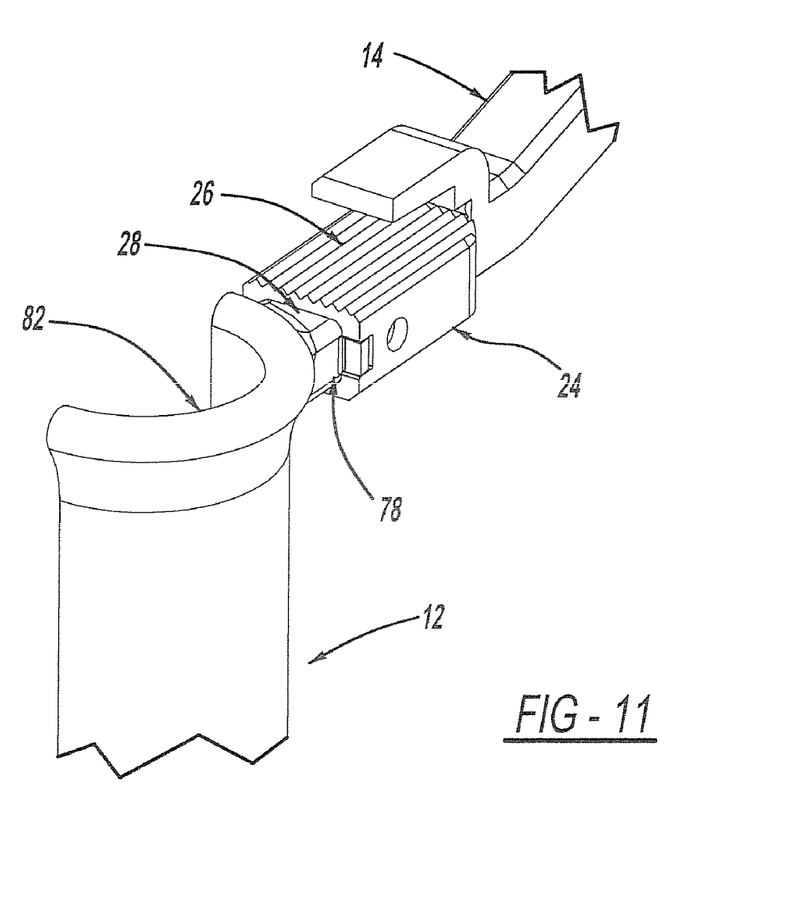
FIG. 11 is a three-dimensional representation of a blade inserted in body module 1.
Figure 12:
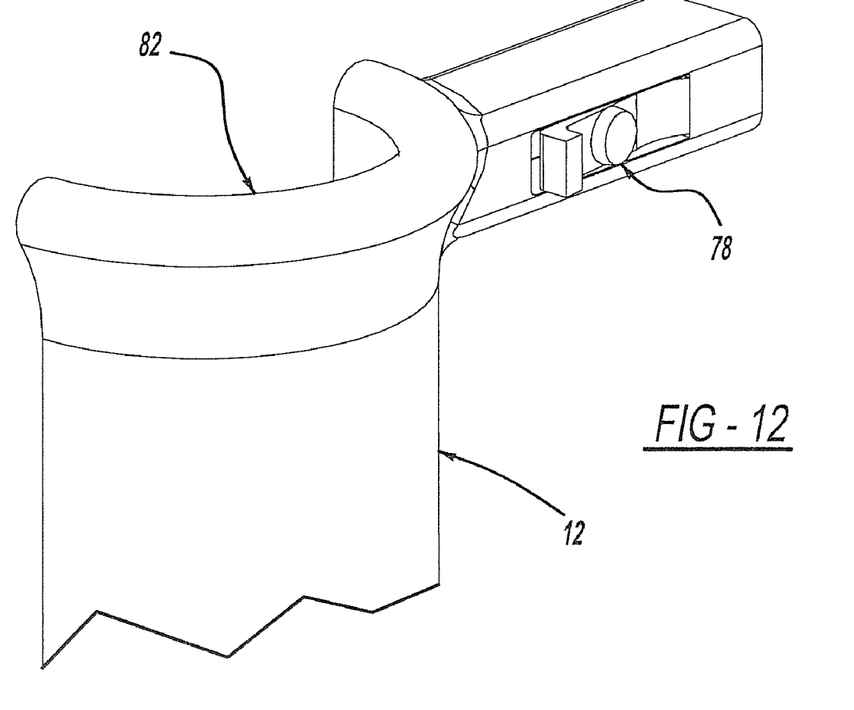
FIG. 12 is a close-up three-dimensional representation of a blade.
Figure 13:
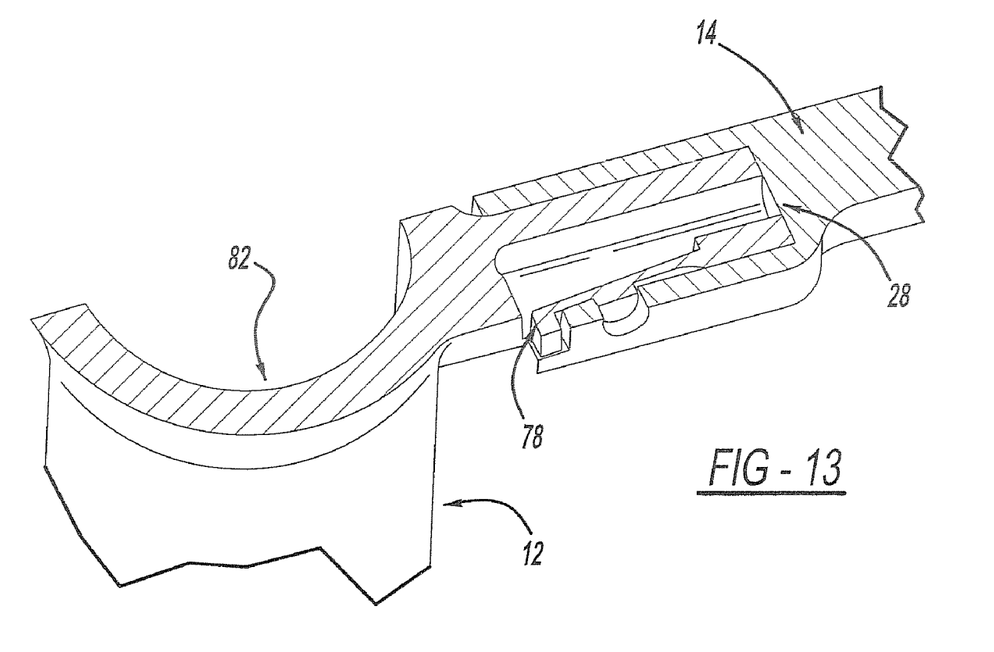
FIG. 13 is a three-dimensional cross-section representation of a blade inserted in body module 1.
Figure 14:
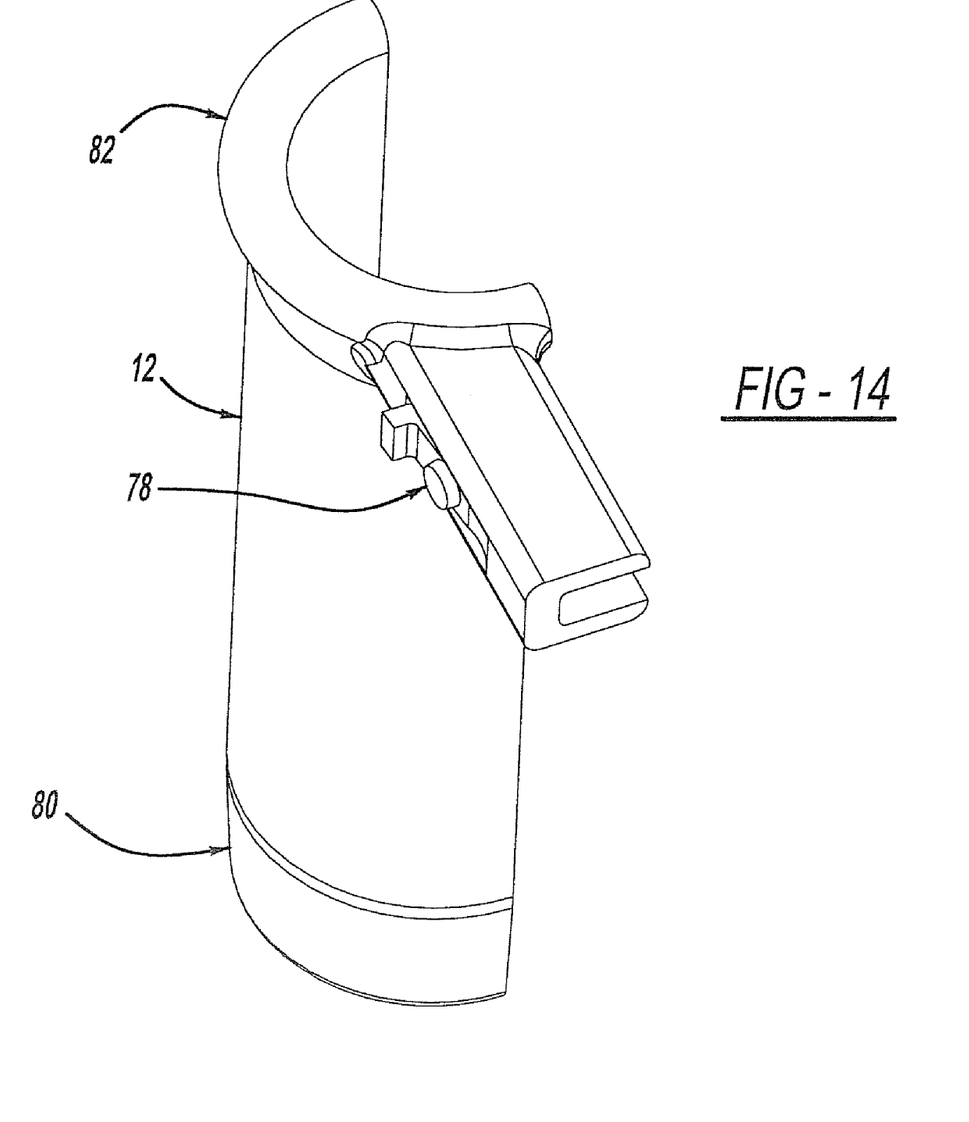
FIG. 14 is a three-dimensional representation of a blade.

Arm 86 can also function as body module 6 as a retractor itself, as shown in FIG. 6. Body module 6 includes the features described above for arm 86. In this embodiment, body module 6 operates in the same manner as retractor 11 (i.e. tubular retraction) described further below.

Blades 12 lock in and out of position in the various slots of the body modules with a locking mechanism 78. For example, the locking mechanism 78 has at least one elastic element that can secure the blade in 26 or 32 when released, and allow the blade be removed when deformed as shown in FIGS. 3 and 8-14. For example, the locking mechanism 78 can operate in the same manner as the end of a phone cord, Ethernet cable, etc. that fits into a phone jack or computer port. Any other suitable locking mechanism can also be used. The blades 12 are made of different biocompatible or non-biocompatible material and can be plastic or metal and are preferably disposable. Alternatively, the blades can be sterilized for subsequent use. The blades 12 can also be transparent (for example, made of plastic) or translucent (for example, made of titanium, or aluminum, etc.) for allowing view of the area retracted under X-ray as in retractors 124, 11, and 25. During spinal surgery, it is very important that the implant and its manipulating instruments surrounded by the blades can be seen during surgery under the X-ray. Most retractors used now are stainless steel, which does not allow such viewing. When blades 12 are transparent, light can be shined directed to the tip or surrounding wall at the blades 12, taking advantage of the non-linear optics of plastic materials, in order to light up the area of the procedure much like an optic fiber. This provides an advantage of reducing the need for a separate light probe being inserted into the surgical site. This feature can be used in any of the methods of use further described below. Different size blades 12 are provided to fit different surgical purposes and sizes of patient being operated on. The blades 12 can also be configured such that they are able to rotate within their slot of the body modules. The distal end 80 of the blade 12 angles outwards compared to the proximal end 82 of the blade 12, which allows for a small incision to be made to insert the retractor and then a larger retraction can be made once the retractor is inside the body. This rotation feature can be included on each of the body modules and used with any of the methods of use further described below. In FIG. 7, slot 100 can be rotated related to part 101 by adjusting part 105 to achieve the above function. Blades 121 can optionally be the same as blades 12 or they can be different, such as utilizing a different attachment mechanism. In each of the modules, the blades 12 can optionally be made to move independently from other blades 12 of the module. In other words, the adjusting mechanisms in each module can be configured such that only one blade moves at a time, instead of two blades 12.

As shown in FIG. 2, each of the body modules 1, 2, 3, 4, and 5 can be connected to obtain different retractors 23, 124, 11, and 25. To make and use retractor 23, the arm 38 of body module 2 is inserted into the slot 50 of the base 46 of body module 3. Blades 121 are attached to slots 44 and 58. Retractor 23 is inserted into a surgical area, and the width of the retraction can be adjusted in one dimension (lateral direction)

to retract tissue by sliding body module 3 along body module 2 with the adjusting mechanism 52, and the position can be locked by activating the locking mechanism 54. After surgery is over, the position can be unlocked, arm 48 of body module 3 slid towards arm 36 of body module 2, and retractor 23 can be removed.

Retractor 124 can be obtained by inserting the arm 38 of body module 2 into the slot 64 of body module 4. The grooved slot 26 of arm 14 of body module 1 is attached to the toothed surface 74 of body module 4. The smooth slot 32 of arm 16 of body module 1 is slidably attached to the smooth surface 76 of body module 4. Blades 12 are attached to slots 28, 34, 44, and 58. Retractor 124 is inserted into a surgical area, and the retraction can be adjusted in two dimensions (lateral and caudal cranial) to retract tissue. This is accomplished by sliding body module 4 along body module 2 with the adjusting mechanism 66 and locking the position by activating the locking mechanism 68 to adjust the retractor in the first dimension. To adjust the retractor in the second dimension, the adjusting mechanism 22 of body module 1 is used to adjust the position of arm 16 along the smooth surface 76 of body module 4. After surgery is over, the positions of body modules 1, 2, and 4 can be unlocked, returned to their previous positions, and retractor 124 can be removed.

Retractor 11 can be obtained by attaching blades 12 to slots 28 and 34 of body module 1. Retractor 11 is inserted into a surgical area, and the retraction can be adjusted tubularly (dilation). For example, a series of dilator tubes 108 with sequentially increasing diameters (starting with a long needle—K-wire) can be used to increase the diameter of the surgical area so that the two blades 12 can be placed sliding along the final dilator tube 108 that has the largest diameter to enter the surgical area. The adjusting mechanism 22 can be used to adjust the space between the arms 14 and 16 and thus creating space between blades 12 in a tubular manner. After surgery is over, the arms 14 and 16 can be brought close together again and retractor 11 can be removed.

Figure 4:
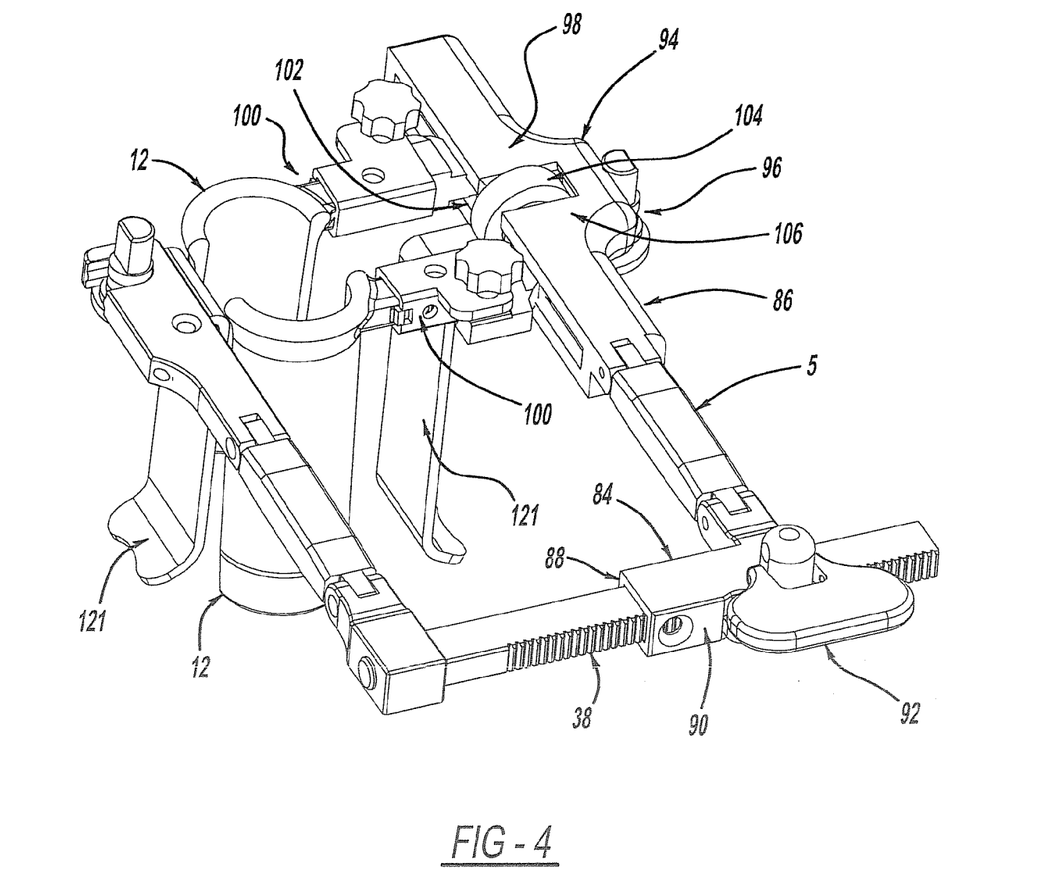
FIG. 4 is a three-dimensional representation of retractor 25 (open)
Figure 5:
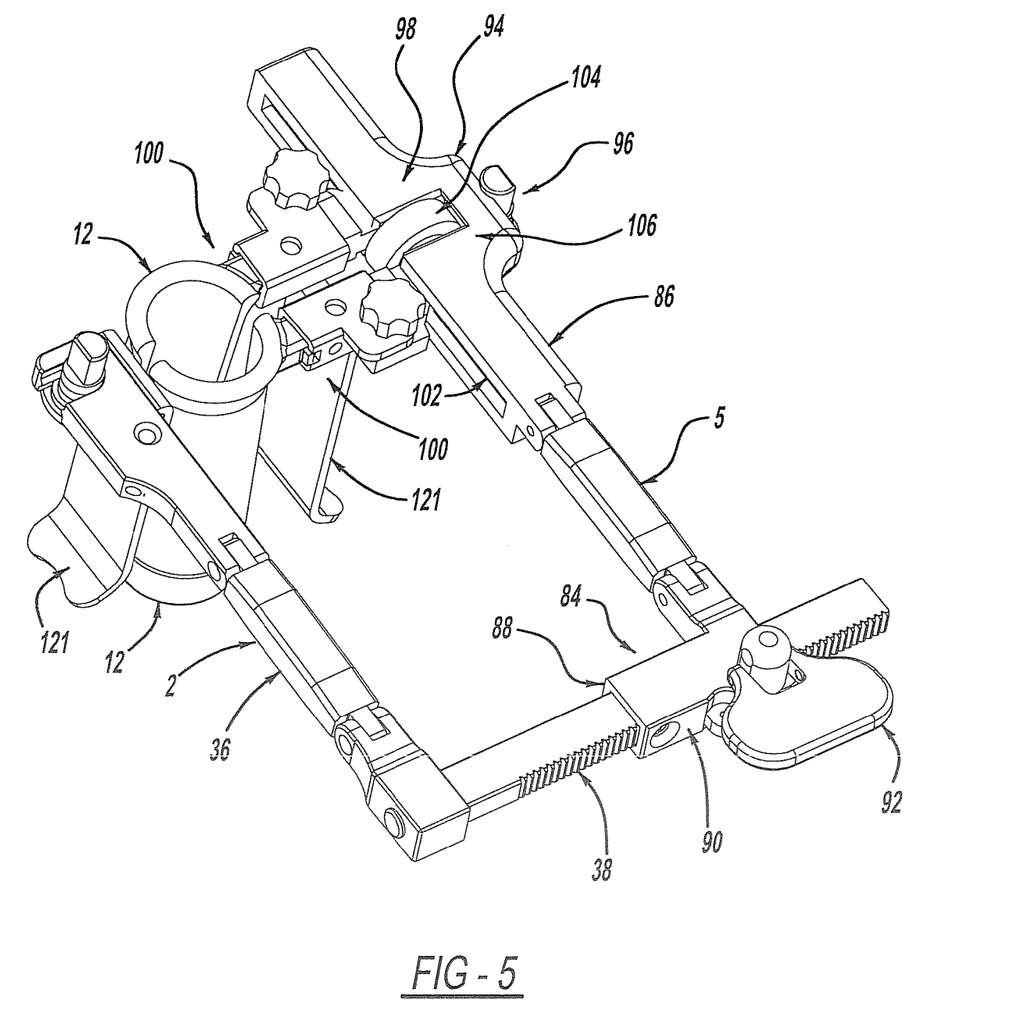
FIG. 5 is a three-dimensional representation of retractor 25 (closed)

To make and use retractor 25, the arm 38 of body module 2 is inserted into the slot 88 of the base 84 of body module 5. Body module 6 is attached to body module 5. Blades 121 are attached to slots 44, 96, and blades 12 are attached to both slots 100 (alternatively both slide mechanisms 100). Retractor 25 is inserted into a surgical area, and retraction can be adjusted in the first dimension to retract tissue by sliding body module 5 along body module 2 with the adjusting mechanism 90, and the position can be locked by activating the locking mechanism 92. Retraction can be adjusted in the second dimension by activating the screw differentiating mechanism 98 by turning the wheel 104 causing screws 102 and 102' to move blades 12 in the blade receiving slots 100 outwards. The position of the blades 12 can be locked with the screw locking mechanism 106. After surgery is over, the positions can be unlocked, arm 86 of body module 5 slid towards arm 36 of body module 2, the blades 12 of the screw differentiating mechanism 98 brought close together, and retractor 25 can be removed. Aspects of the operation of retractor 25 that are specific to body module 5 also apply to body module 6 when it is a retractor itself; however, blade 121 in slot 96 can be optionally removed from this embodiment so that only blades 12 are present.

In each of the modules, various parts can be automated for ease of operation during a surgical procedure. For example, obtaining any position of the blades 12 in each of the modules can be automated with a computer or an electric or pneumatic mechanism. Also, adjustment of the position of each of the body modules and various arms can be automated. In essence, any part of the module that can be adjusted by a surgeon can optionally be adjusted through an automated mechanism.

Each of the retractors can also include a mounting mechanism 120 for attaching various tools and instruments needed during surgery in order to free up the surgeon's hands to perform procedures. The mounting mechanism 120 can be operatively attached to any suitable place on the retractors so that the tools and instruments are accessible in the site of surgery. One example of placement of the mounting mechanism 120 is shown in FIG. 6. Tools and instruments that can be mounted, include, but are not limited to, suction/irrigation, fiber optic lights, fluid delivery tubes, and endoscopes.

There are several advantages to the modular retractor system 10 of the present invention. It is a compact, modular, and versatile kit that can be used for minimally invasive surgery or any surgery requiring a retractor. Preferably, the modular retractor system 10 is used for different surgeries including spine surgery. The system 10 can be easily configured and used by all surgeons to his/her preferred familiar module that he/she was previously trained. As mentioned above, the system 10 is easy to use and configure as it can be color coded. The reconfigurable modular kit with disposable blades 12 of different length sizes make the size of the system 10 very compact so that it is easy for hospitals and surgical centers to store the system 10. The disposable blades 12 reduce the risk of cross contamination much like the disposable needle has done. When the blades 12 are in translucent or transparent form, they allow for the surgeon to have a clear view of the surgical area under X-ray, so that they can position and manipulate the implant in the best anatomic position of patient surrounded by the retractor. Standard stainless steel blades of current retractors block the view under X-ray. Furthermore, the blade locking mechanism 78 allows for quick and easy attachment and detachment of blades 12. Transparent plastic blades can even allow the view of tissue, a feature that the surgeon would feel like nothing is block his/her view in surgery.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The invention claimed is:

1. A reconfigurable modular retractor system comprising:
an interchangeable first body module including a first arm and a second arm operatively connected at a proximal end by a connecting mechanism, an adjusting mechanism adjustably connected to said arms, said first arm having a distal end including a grooved slot, said grooved slot receiving a toothed surface of an interchangeable fourth body module and a blade receiving slot, said second arm having a distal end including a smooth slot, said smooth slot receiving a smooth surface of said fourth body module and a blade receiving slot;
an interchangeable second body module including a first arm and a second arm perpendicular thereto operatively connected at a proximal end, said first arm having a distal end including a blade receiving slot, said second arm being toothed;

an interchangeable third body module including a base perpendicular to an arm, said base including a slot, said slot receiving said second arm of said second body module and an adjusting mechanism that adjusts said third body module along said second arm of said second body module, said adjusting mechanism including a locking mechanism that maintains a position of said third body module along said second body module, said arm having a distal end including a blade receiving slot;

said interchangeable fourth body module including a base perpendicular to an arm, said base including a slot, said slot receiving said second arm of said second module and an adjusting mechanism that adjusts said fourth body module along said second body module, said adjusting mechanism including a locking mechanism that maintains a position of said fourth body module along said second body module, said arm having a distal end including a blade perpendicular and angled backward thereto, a toothed surface below said distal end, and a smooth surface operatively attached above said distal end; and an interchangeable fifth body module including a base perpendicular to and removably attached to an arm, said base including a slot, said slot receiving said second arm of said second body module and an adjusting mechanism that adjusts said fifth body module along said second body module, said adjusting mechanism including a locking mechanism that maintains a position of said fifth body module along said second body module, said arm having a distal end including a blade receiving slot and a screw differentiating mechanism, said screw differentiation mechanism including a second blade receiving slot moveably attached along a right hand screw and a third blade receiving slot moveably attached along a left hand screw, a wheel that rotates said screws and moving said second and third blade receiving slots, and a blade receiving slot locking mechanism that maintains a position of said second and third blade receiving slots.

2. The retractor system of claim 1, wherein said arm is a sixth body module.

3. A retractor including the sixth body module of claim 2.

4. The retractor system of claim 1, wherein said connecting mechanism is chosen from the group consisting of a screw or a pin.

5. The retractor system of claim 1, wherein said adjusting mechanism of said first body module is a winged screw.

6. The retractor system of claim 1, wherein said adjusting mechanisms of said third, fourth, and fifth body modules are pinions, and said locking mechanisms are wings.

7. The retractor system of claim 1, wherein said adjusting mechanisms move said blade receiving slots independently of each other.

8. The retractor system of claim 1, further including in said blade receiving slots blades.

9. The retractor system of claim 8, wherein said blades include blade locking mechanisms that lock in said blade receiving slots.

10. The retractor system of claim 9, wherein said blade locking mechanisms include at least one elastic element that secures said blades when released and for allowing removal of said blades when deformed.

11. The retractor system of claim 10, wherein said blade locking mechanism is chosen from the group consisting of a phone cord end and an Ethernet cable end.

12. The retractor system of claim 8, wherein said blades are disposable.

13. The retractor system of claim 8, wherein said blades are transparent and made from plastic.

14. The retractor system of claim 13, wherein said blades include a lighting mechanism that lights up said blades when light is shined thereupon.

15. The retractor system of claim 8, wherein said blades are translucent and made from a material chosen from the group consisting of titanium and aluminum.

16. The retractor system of claim 8, wherein said blades are rotatable within said blade receiving slots.

17. The retractor system of claim 1, further including a mounting mechanism operatively attached to said body modules that mounts tools and instruments.

18. A retractor including the second body module and third body module of claim 1.

19. A retractor including the first body module, second body module, and fourth body module of claim 1.

20. A retractor including the first body module of claim 1.

21. A retractor including the second body module and fifth body module of claim 1.

22. A method of using the retractor system of claim 1, including the steps of:
    forming a retractor by using at least one body module;
    attaching blades to the body module;
    inserting the retractor into a surgical area;
    retracting tissue;
    removing retraction from the tissue; and
    removing the retractor.

23. The method of claim 22, wherein said retracting step is further defined as retracting tissue in one direction using a retractor formed from the second and third body module.

24. The method of claim 22, wherein said retracting step is further defined as retracting tissue in two directions using a retractor formed from the first, second, and fourth body modules.

25. The method of claim 22, wherein said retracting step is further defined as retracting tissue tubularly using a retractor formed from the first body module.

26. The method of claim 22, wherein said retracting step is further defined as retracting tissue in two directions using a retractor formed from the second and fifth body modules.

27. The method of claim 22, wherein said retracting step is further defined as retracting tissue tubularly using a retractor formed from the sixth body module in claim 2.

28. The method of claim 22, further including the step of viewing the surgical area under X-ray wherein the retractor includes blades comprising material chosen from translucent and transparent.

29. The method of claim 28, further including the step of shining light on the blades and lighting up the surgical area.

* * * * *